United States Patent [19]

Stromgren et al.

[11] Patent Number: 4,962,768
[45] Date of Patent: Oct. 16, 1990

[54] STIRRUP-LOCK ANKLE SUPPORT

[75] Inventors: Lawrence T. Stromgren, 2916 Hillcrest, Hays, Kans. 67601; George P. Kamau, III, Sterling, Va.

[73] Assignee: Lawrence Thompson Stromgren, Hays, Kans.

[21] Appl. No.: 243,263

[22] Filed: Sep. 12, 1988

[51] Int. Cl.⁵ .............................................. A61F 5/00
[52] U.S. Cl. ................................... 128/80 H; 128/166
[58] Field of Search ............................. 128/80 H, 166

[56] References Cited

U.S. PATENT DOCUMENTS

| | | | |
|---|---|---|---|
| 1,374,669 | 4/1921 | McLellan | 182/166 |
| 1,389,767 | 9/1921 | Ludwig | 128/166 |
| 1,717,609 | 6/1929 | Ludwig | 128/166 |
| 2,539,170 | 1/1951 | Waite et al. | 128/166.5 |
| 3,073,305 | 1/1963 | Biggs | 128/166 |
| 3,506,000 | 4/1970 | Baker | 128/166 |
| 4,166,406 | 9/1979 | Applegate | 128/80 H |

Primary Examiner—Edgar S. Burr
Assistant Examiner—Huong Q. Pham
Attorney, Agent, or Firm—D. A. N. Chase; Joan Optican Herman

[57] ABSTRACT

A reusable ankle support for providing support to the ankle region comprises a socklike elastic sheath with a pair of crossed elongated elastic straps attached thereto. After the sheath is positioned on the foot of the wearer, the straps are wrapped around the ankle in a predetermined manner, and thereby present a pair of stirrups. Stretch locks limit the amount of stretch which may be pulled from the stirrups. The stirrup-lock system and the relative positioning of the straps on the ankle provide support to the lower region of the ankle to thereby help prevent low sprains.

5 Claims, 2 Drawing Sheets

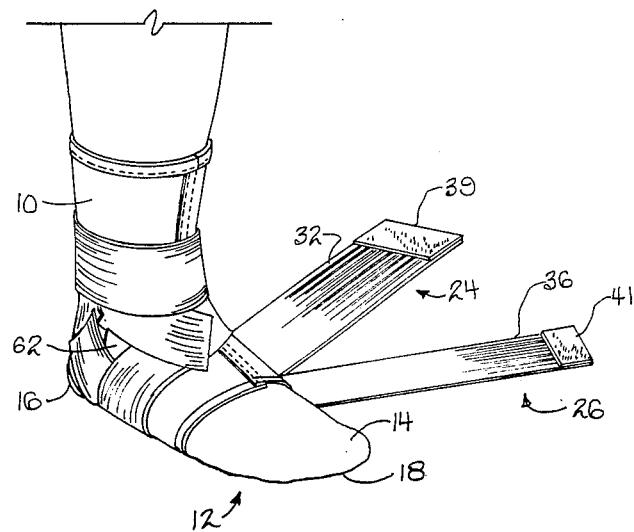
Fig. 1.
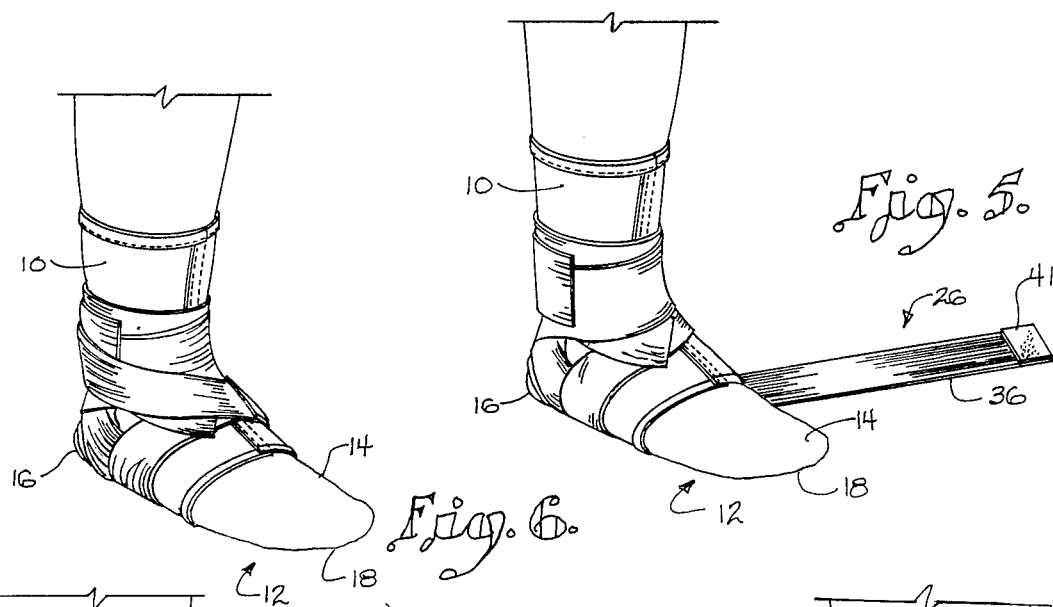
Fig. 5.
Fig. 6.
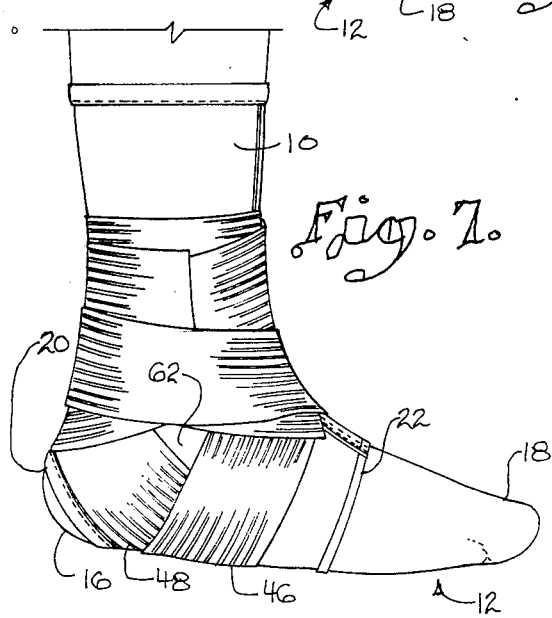
Fig. 7.
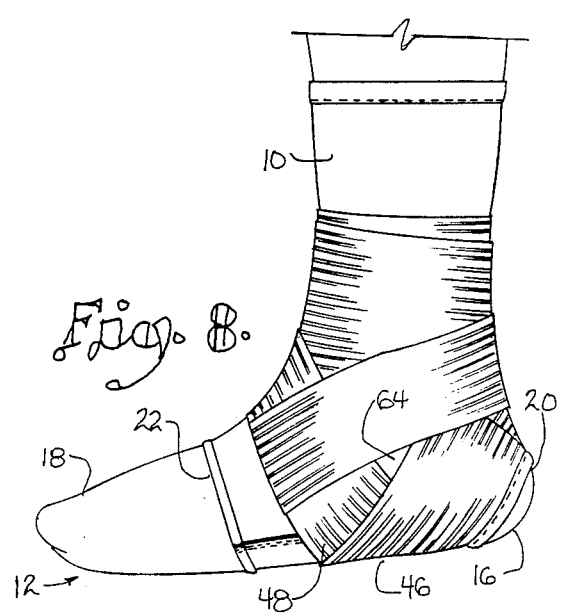
Fig. 8.

4,962,768

STIRRUP-LOCK ANKLE SUPPORT

BACKGROUND OF THE INVENTION

This invention relates to improvements in ankle supports and, in particular, to a support which is capable of enhancing the stability of both the medial and lateral sides of the ankle joint with stirrups and stretch-locks. This invention further relates to a reusable ankle support which may be worn interchangeably on either the right ankle or the left ankle.

Ankle supports and taping of the ankle are commonly used to prevent or reduce the severity of debilitating ankle sprains. Several methods of wrapping are available in various ankle supports, either using adhesive tape strapping or reusable canvas-type ankle wraps. Ankle wraps are applied to virtually immobilize the contact between the bones and the ligaments of the ankle region in order to prevent injurious pulling, stretching, or tearing of these ligaments.

Adhesive tapes, however, can be expensive to use, both because they are not reusable and because of the manpower costs involved in properly taping or supervising the taping of an ankle. Furthermore, tape has a tendency to loosen during use. Reusable ankle wraps are a solution to these problems, but most of these wraps are not developed to specifically protect against low sprains, which are injuries to ligaments below the lateral malleolus of the fibula and the medial malleolus of the tibia, often referred to as the "ankle bones."

Consequently, the present invention utilizes a reusable ankle wrap which enhances the stability of both the medial and lateral sides of the ankle joint. Additionally, the stirrup-lock design provides double elastic stirrups positioned under the foot, and stretch locks which enable the stretch to be pulled from the stirrups to render them substantially inflexible. The stirrup-locks provide strength without affecting circulation or comfort. This design prohibits sprains below the lateral malleolus and the medial malleolus. Furthermore, this support may be interchangeably used with either the right or the left leg of a wearer without modification.

OBJECTS OF THE INVENTION

It is, therefore, an important object of the present invention to provide an ankle support which locks the ankle from abnormal rotations that injure both the medial and lateral sides of the ankle joint.

It is another important object of the present invention to provide an improved reusable ankle support, as aforesaid, which offers support to the ankle ligaments below the lateral malleolus and the medial malleolus.

It is a further important object of the present invention to provide an ankle support, as aforesaid, which presents stirrups to enhance the stability of the ankle joint.

It is yet another important object of the present invention to provide an ankle support as aforesaid, which presents stretch locks to limit the flexibility of the stirrups to provide strength without affecting circulation or comfort.

BRIEF DESCRIPTION OF THE DRAWINGS

FIGS. 3 through 6 show, in order, the steps of the predetermined method of wrapping the ankle and are as follows:

FIG. 3 is a perspective view, taken from the outside of the right foot and showing the socklike sheath slipped over the foot of a wearer, with the outside portion of one strap in operative position.

FIG. 4 is a perspective view similar to FIG. 3, showing the ankle support with the outside portions of both straps in operative position.

FIG. 5 is a perspective view similar to FIGS. 3 and 4, showing the ankle support with the outside portions of both straps and the inside portion of one strap in operative position.

FIG. 6 is a perspective view similar to FIGS. 3 through 5, showing the ankle support with both straps in operative position.

FIG. 7 is an elevational view taken from the outside of the right foot showing the ankle support in a fully secured position on the right foot of the wearer, and further showing the positioning of the stirrup portions below the lateral malleolus.

FIG. 8 is an elevational view as in FIG. 7, taken from the inside of the ankle support and showing the positioning of the stirrup portions below the medial malleolus.

DETAILED DESCRIPTION OF THE PREFERRED EMBODIMENT

Figure 1:
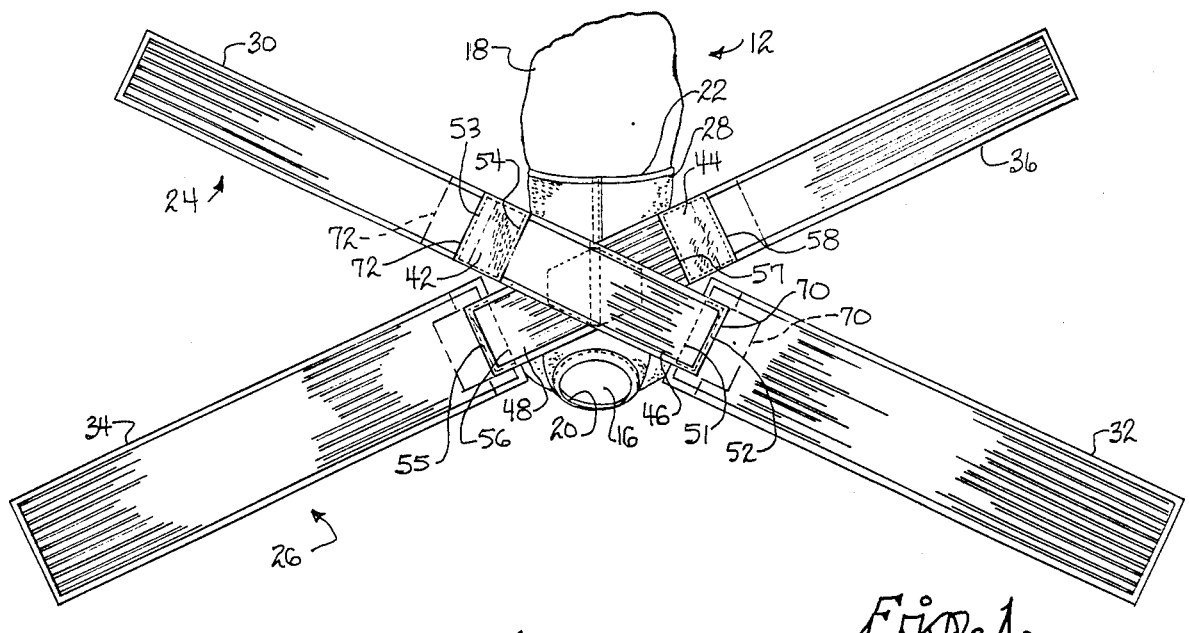
FIG. 1 is a bottom plan view of the ankle support of the present invention shown on the right foot of a wearer, with neither of the straps in their operative positions. The broken lines depict the degree of stretch which can be achieved from the stirrup portions.
Figure 2:
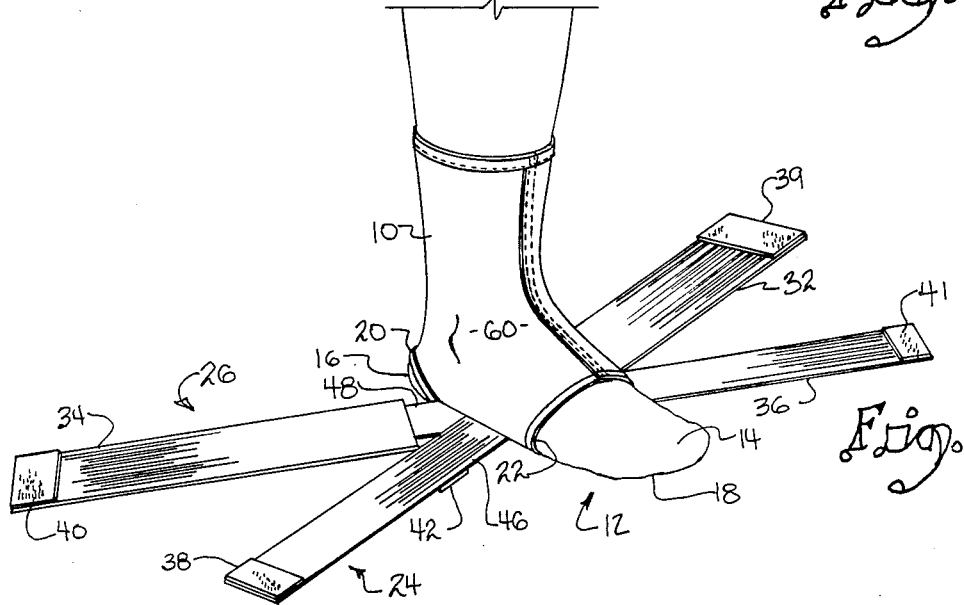
FIG. 2 is a perspective view taken from the outside of the right foot and showing the ankle support on the ankle of a wearer, with neither of the straps in operative positions.
Figure 3:
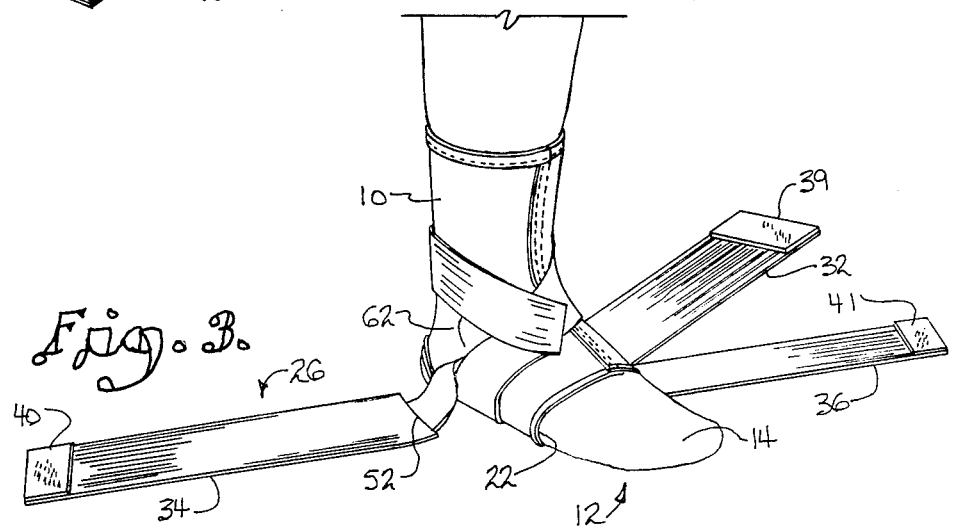

A tubular, elastic sheath, broadly denoted 10, receives the leg of a wearer, as is clear in the drawings, and is slipped over the foot 12 of the wearer, the foot 12 preferably having an athletic sock 14 thereon. Upon fitting, the heel 16 and toe 18 regions of the foot 12 protrude through the sheath openings 20 and 22, respectively, as shown in FIG. 1. The sheath 10 is made of an elastic fabric such as Spandex or the like, and is sized to have an unstretched diameter somewhat less than the wearer's leg so that the fabric is stretched as it is pulled over the foot 12 into position. This holds the sheath 10 in place and also imparts some support to the ankle region.

Two elongated elastic straps 24 and 26 are crossed under the bottom portion 28 of the sheath 10 and anchored, preferably at the intersection thereof, to the sheath 10 by stitching or the like. The straps 24 and 26 are longitudinally stretchable, and are placed in tension as they are drawn into their respective operative positions as illustrated. The opposed ends 30 and 32 of strap 24 are provided with corresponding fasteners 38 and 39. The fasteners 38 and 39 are adapted to mate with strap 24, as well as with fastener 42 which is disposed intermediate ends 30 and 32 of strap 24, and are made of VELCRO or the like. Likewise, opposed ends 34 and 36 of strap 26 are provided with corresponding fasteners 40 and 41, which are adapted to mate with strap 26, as well as with VELCRO fastener 44 which is disposed intermediate ends 34 and 36 of strap 26.

Each strap 24 and 26 has a central stirrup portion 46 and 48, respectively. Stirrup portion 46 terminates at corresponding stretch locks, one of which comprises parallel transverse lines of stitching 51 and 52 located adjacent one end thereof and forming a joint at which stirrup portion 46 is attached to the wider, outer segment of strap 24 that presents end 32. The other stretch lock is provided by an inelastic spacer (fastener 42) located adjacent the other end thereof and secured thereto by parallel transverse lines of stitching 53 and 54. It may be appreciated that in the preferred embodiment, VELCRO fastener 42 also serves as the spacer. Likewise, stirrup portion 48 has corresponding stretch locks which are comprised of similarly situated inelastic elements, i.e., parallel transverse lines of stitching 55 and 56 forming a joint, and an inelastic spacer (fastener 44) that is secured to strap 26 by parallel transverse lines of stitching 57 and 58.

The stirrup portions 46 and 48 are made of an elastic material with a relatively low stretch factor. The respective inelastic stretch locks serve to isolate these stirrup portions 46 and 48 from the outer portions of straps 24 and 26, and thus enable the stretch to be pulled from the stirrup portions 46 and 48 when force is applied to the straps 24 and 26 as they are placed in operative position. The phantom lines in FIG. 1 show the amount of stretch which may be achieved from the stirrup portion 46, as the terminal end 70 of stirrup portion 46 can be displaced as shown. Likewise, the terminal end 72 of spacer 42 can be displaced to the maximum shown by the phantom lines. The amount of stretch which may be achieved from stirrup portion 48 is similarly shown by phantom lines. The stirrup portions 46 and 48 preferably have a relatively low stretch factor of approximately 30%.

In operation, the sheath 10 is slipped over the ankle of the wearer as described above. The manner of wrapping the ankle support is depicted in FIGS. 2 through 6. Initially, straps 24 and 26 extend outwardly from the sheath 10 in an X-shaped configuration. End 30 of strap 24 is drawn in front of the ankle 60 region (across the tibia) and to the rear thereof. It is then drawn across the fibula to the front of the ankle 60 where fastener 38 mates with fastener 42, or with strap 24 to secure the same in operative position. It is apparent from FIG. 3 that end 30 of strap 24 is operatively positioned above the lateral malleolus 62 of the fibula. Next, end 34 of strap 26 is drawn behind the ankle 60 region and then around the front of the ankle 60. Fastener 40 mates with strap 26 to thereby secure the strap 26 in operative position. As can be seen from FIG. 4, the straps 24 and 26 are positioned above and below the lateral malleolus 62.

End 32 of strap 24 is then placed into operative position by drawing it behind the ankle 60 and across the fibula to the front of the ankle 60 where strap 24 is secured by mating fastener 39 with strap 24. Finally, end 36 of strap 26 is drawn in front of the ankle 60, across the fibula, and to the rear thereof. It is then drawn across the tibia to the front of the ankle 60 where fastener 41 mates with fastener 44, or with strap 26 to secure the same in operative position. Straps 24 and 26 are drawn into operative position and disposed either above or below the lateral malleolus of the fibula and the medial malleolus of the tibia, as is apparent in FIGS. 7 and 8, wherein the ankle support is shown in fully operative position.

Upon conclusion of the wrapping, as shown in FIGS. 7 and 8, the wearer is provided with a pair of crossed stirrups 46 and 48 which enhance the stability of both the medial and lateral sides of the ankle 60 region. The V-shaped configuration formed from the positioning of the stirrups 46 and 48 below the lateral malleolus 62 and the medial malleolus 64 prevents low sprains. In use, the above described stretch locks of stirrups 46 and 48 enable the stretch to be pulled from the stirrups as the straps 24 and 26 are drawn into operative position. With this stirrup-lock mechanism, the straps 24 and 26 are able to securely support the ankle and protect it against abnormal rotation. Furthermore, when the stirrups 46 and 48 are fully stretched and relatively inflexible, they are adapted to fit snugly below the lateral malleolus and the medial malleolus to thus prohibit low sprains.

Although the ankle support is described for use with the right foot, it is understood that it may be interchangeably used with the left foot without any modifications. The manner of wrapping is simply reversed. Accordingly, it is understood that this ankle support can be used for either foot with identical accompanying advantages and results.

It is to be understood that while certain forms of this invention have been illustrated and described, it is not limited thereto, except in so far as such limitations are included in the following claims.

Having thus described the invention, what is claimed as new and desired to be secured by Letters Patent is:

1. An ankle support comprising:
   a tubular elastic sheath adapted to receive either ankle of a wearer and to be positioned over the ankle,
   a pair of crossed, elongated elastic straps each having opposed first and second end portions, each of said straps comprising a pair of relatively elastic outer segments presenting said first and second end portions respectively and an intermediate stirrup segment made of elastic material with a relatively low stretch factor,
   stretch locking means associated with each of said straps and interconnecting said outer segments with said intermediate stirrup segment,
   means anchoring each of said crossed straps intermediate said stirrup segment thereof to said sheath on a bottom portion thereof adapted for disposition underneath the foot of a wearer,
   fastener means on respective end portions of said straps,
   said straps in use being drawn around said sheath into operative position, crossing each other below the ankle bone of the wearer and being secured in said operative positions by said fastener means,
   said straps and said associated stirrup segments in their operative positions presenting an essentially V-shaped configuration for supporting both the medial and lateral sides of the ankle to restrict both medial and lateral movement thereof, and
   said stretch locking means isolating said stirrup segments from said outer segments and limiting the elasticity of said stirrup segments to cause said stirrup segments to become substantially longitudinally inflexible below the ankle bone when said straps are drawn around the ankle into their operative positions.

2. The ankle support as claimed in claim 1, wherein said crossed straps are anchored at the region of intersection thereof.

3. The ankle support as claimed in claim 2, wherein said stirrup segments are positioned at the region of intersection of said crossed straps.

4. The ankle support as claimed in claim 2, said stretch locking means comprising an inelastic element between each of said outer segments and a corresponding end of said associated stirrup segment.

5. The ankle support as claimed in claim 1, wherein said stretch locking means comprise relatively inelastic portions adjacent the longitudinal ends of said stirrup segments.

* * * * *